(12) United States Patent
Holzer

(10) Patent No.: US 8,097,602 B1
(45) Date of Patent: Jan. 17, 2012

(54) METHOD OF TREATING BODY INSECT INFESTATION

(75) Inventor: David Holzer, Miami Beach, FL (US)

(73) Assignee: Host Pharmaceuticals, LLC, Hillsdale, NJ (US)

( * ) Notice: Subject to any disclaimer, the term of this patent is extended or adjusted under 35 U.S.C. 154(b) by 748 days.

(21) Appl. No.: 12/035,507

(22) Filed: Feb. 22, 2008

(51) Int. Cl.
*A01N 55/00* (2006.01)
*A01N 37/00* (2006.01)
*A01N 27/00* (2006.01)

(52) U.S. Cl. .......................... 514/63; 514/560; 514/762

(58) Field of Classification Search .................. None
See application file for complete search history.

(56) References Cited

U.S. PATENT DOCUMENTS

| 5,288,483 A | 2/1994 | Cardin et al. |
| 2003/0013683 A1 | 1/2003 | Holzer et al. |

OTHER PUBLICATIONS http://www.scienceinthebox.com/en_UK/glossary/surfactants_en.html: from Procter and Gamble, 2005.*

* cited by examiner

*Primary Examiner* — Shanon A Foley
(74) *Attorney, Agent, or Firm* — Stroock & Stroock & Lavan LLP

(57) ABSTRACT

Described is a safe and effective method for treating lice and nits (fleas, ticks and other insects) with a low surface tension chemical formulation.

18 Claims, No Drawings

US 8,097,602 B1

METHOD OF TREATING BODY INSECT INFESTATION

FIELD OF THE INVENTION

This invention relates to the safe and effective treatment of lice, nits (and other infestational insects) by using low surface tension chemical formulations.

BACKGROUND OF THE INVENTION

For centuries, people have been plagued by head lice, body lice, and pubic lice, which appear in numerous species all having similar physiological characteristics. Over the years, people have expended tremendous efforts and resources to develop a safe and effective method for eliminating the problem of lice and nits. To date, the only patented processes for killing lice and nits involve the use of poisons, pesticides or noxious soaps with numerous side effects and cautionary uses. These pediculicides, such as lindane, pyrethrum, or malathion, are not optimal for the treatment of lice or nits because they are not healthful, and because, over time, lice tend to develop a natural resistance to poison or pesticide formulation.

SUMMARY OF THE INVENTION

It is accordingly an object of the present invention to provide a method and chemical formulation for effective yet safe treatment for body insect infestation such as lice, fleas, and the like.

Generally present the invention compromises the direct treatment of body insect infestation with a chemical formulation to effectively kill infesting insects such as lice, and nits, as well as fleas, ticks and other insects. In accordance with the present invention, there is provided a method of treating body insect infestation comprising: topically applying a chemical formulation comprising propoxytetramethyl piperidinyl dimethicone, C-11 pareth-7 and trideceth-6 to the body infestation; and allowing the chemical formulation to remain on the insect infestation for a time sufficient to achieve at least 80% insect mortality. The chemical formulation may have a surface tension below about 25 dynes/centimeter at 20° C. and a viscosity above about 200 centistokes.

In accordance with another embodiment of the present invention there is provided a method of treating body insect infestation comprising: topically applying a chemical formulation comprising about 17.5 to 40% by volume of a siloxane, wherein the chemical formulation has a surface tension below about 25 dynes/centimeter at 20° C. and a viscosity above about 200 centistokes to the body infestation; and allowing the chemical formulation to remain on the insect infestation for a time sufficient to achieve at least 80% insect mortality. The chemical formulation may further comprise additives capable of evaporation such that the resulting siloxane concentration following evaporation of the additives is about 17.5 to 40% by volume.

DETAILED DESCRIPTION OF THE INVENTION

It is accordingly an object of the present invention to provide a method and chemical formulation for effective yet safe treatment for body insect infestation such as lice, fleas, and the like.

In accordance with an embodiment of the present invention, there is provided a chemical formulation comprising at least 3% by volume of a siloxane, wherein the resulting liquid formulation has a surface tension below 25 dynes/cm at 20° C. and a viscosity above 200 centistokes (cst). In accordance with yet another embodiment of the present invention, there is provided a chemical formulation comprising a combination of two or more siloxanes wherein the resulting total siloxane concentration is at least 3% by volume of siloxane and wherein the resulting liquid formulation has a surface tension below 25 dynes/cm at 20° C. and a viscosity above 200 cst.

The chemical formulation may further comprise one or more surfactants, including, but not limited to, non-ionic surfactants, anionic surfactants, amphoteric surfactants or a mixture thereof. Non-limiting examples of non-ionic surfactants include: Capryleth-n, where n=4, 5; Deceth-n, where n=3, 4, 5, 6, 8, 9, 10; Undeceth-n, where n=3, 5, 7, 8, 9, 11; Coceth-n, where n=3, 5, 7, 8, 10; C9-11 Pareth-n, where n=5, 6, 8; C9-15 Pareth-8; C11-15 Pareth-n, where n=3, 5, 9, 12, 15, 20, 30, 40; C11-21-Pareth-n, where n=3, 10; C12-1-n, where n=3, 5, 7, 9, 12; C12-14 Pareth-n, where n=5, 7, 9, 12; C12-15 Pareth-n, where n=2, 3, 4, 5, 7, 9, 10, 11, 12; C12-16 Pareth-n, where n=5, 7, 9; C14-15 Pareth-n, where n=4, 7, 8, 11, 12, 13; C20-22 Pareth-30; C20-40 Pareth-n, where n=3, 10, 24, 40; C22-24 Pareth-33; C30-50 Pareth-n, where n=3, 10, 40; C40-60 Pareth-n, where n=3, 10; C12-14 Sec-Pareth-5; C12-14 Sec-Pareth-n, where n=8, 9, 15, 20, 30, 40, 50; C11-15 Sec-Pareth-12; Dihydrocholeth-n, n=15, 20, 30; Glycereth-n, where n=7, 12, 20, 26, 31; Hydrogenated Talloweth-n, where n=12, 25; Isoceteth-n, where n=10, 15, 20, 30; Isodeceth-n, where n=4, 5, 6; Isolaureth-n, where n=3, 6, 10; Isosteareth-n, where n=2, 3, 10, 12, 20, 22, 25, 50; Laneth-n, where n=5, 10, 15, 16, 20, 25, 40, 50, 60, 75; Laureth-n, where n=1, 2, 3, 4, 5, 6, 7, 8, 9, 10, 11, 12, 13, 14, 15, 16, 20, 21, 23, 25, 30, 40, 50; Myreth-n, where n=2, 3, 4, 5, 10; Octyldodeceth-n, where n=5, 10, 16, 20, 25, 30; Oleth-n, where n=2, 4, 5, 6, 7, 8, 9, 10, 11, 12, 15, 16, 20, 23, 24, 25, 30, 35, 40, 44, 50, 106; PPG-2-Ceteareth-9; PPG-4-Ceteareth-12; PPG-10-Ceteareth-20; PPG-1-Ceteth-n, where n=1, 5, 10, 20; PPG-2-Ceteth-n, where n=1, 5, 10, 20; PPG-2-Ceteth-n, where n=5, 10, 20; PPG-4-Ceteth-n, where n=1, 5, 10, 20; PPG-5-Ceteth-20; PPG-8-Ceteth-n, where n=1, 2, 5, 10; PPG-n Cetyl Ether, where n=10, 20, 28, 30, 50; PPG-2 C12-15 Pareth-6; PPG-4 C13-15 Pareth-15; PPG-5 C9-15 Pareth-6; PPG-6 C9-11 Pareth-n, where n=5, 12, 11; PPG-3 C12-14 Sec-Pareth-7; PPG-4 C12-14 Sec-Pareth-5; PPG-5 C12-14 Sec-Pareth-7; PPG-5 C12-14 Sec-Pareth-9; PPG-1-Deceth-6; PPG-2-Deceth-10; PPG-4-Deceth-n, where n=4, 6; PPG-6-Deceth-n, where n=4, 9; PPG-8 Deceth-6; PPG-14 Deceth-6; PPG-6-Decyltetradeceth-n, where n=12, 20, 30; PPG-13 Decyltetradeceth-24; PPG-20-Decyltetradeceth-10; PPG-9-Ethylhexeth-5; PPG-20-Glycereth-30; PPG-24-Glycereth-24; PPG-66-Glycereth-12; PPG-2-Isodeceth-n, where n=4, 6, 9, 12; PPG-3-Isodeceth-n, where n=1, 9; PPG-3-Isosteareth-9; PPG-12-Laneth-50; PPG-3-Laureth-9; PPG-4 Laureth-n, where n=2, 5, 7; PPG-6-Laureth-3; PPG-25-Laureth-25; PPG-9-Steareth-3; PPG-23-Steareth-34; PPG-30 Steareth-4; PPG-34-Steareth-3; PPG-1 Trideceth-6; PPG-4 Trideceth-6; PPG-6 Trideceth-8; Sorbeth-n, where n=6, 20, 30, 40; Tocophereth-n, where n=5, 10, 12, 18, 50; Trideceth-n, where n=2, 3, 5, 6, 7, 8, 9, 10, 11, 12, 15, 18, 20, 21, 50; Ceteth-n, where n=1, 2, 3, 4, 5, 6, 7, 10, 12, 14, 15, 16, 17, 18, 20, 23, 24, 25, 30, 40, 45; Ceteareth-n, where n=3, 4, 5, 6, 7, 8, 9, 10, 11, 12, 13, 14, 15, 16, 17, 18, 20, 22, 23, 24, 25, 27, 28, 29, 30, 33, 34, 40, 50, 55, 60, 80, 100; Cetoleth-n, where n=6, 10, 11, 15, 20, 22, 24, 25, 30; Choleth-n, where n=5, 10, 15, 20, 24, 30; Steareth-n, where n=2, 3, 4, 5, 6, 7, 8, 10, 11, 13, 14, 15, 16, 20, 21, 25, 27, 30, 40, 50, 80, 100; and Beheneth-n, where n=5, 10, 20, 25, 30.

Non-limiting examples of anionic surfactants which may be employed as emulsifiers include: Alkyl ether sulfates, Alkyl sulfates, α-Olefin sulfonates, sulfocuccinates, Alkyl isethionates, Acyl amides, Acyl peptides, Alkyl ether carboxylates, Alkyl phosphates, Acylamphoglycinates, Acylamphopropionates and Amine oxides, Ammonium C12-15 Alkyl Sulfate, Ammonium Capryleth Sulfate, Ammonium Coco-Sulfate, Ammonium C12-15 Pareth Sulfate, Ammonium Laureth-n Sulfate, where n=3, 5, 7, 9, 12; Ammonium Lauryl Sulfate, Ammonium Myreth Sulfate, Ammonium Myristyl Sulfate, Ammonium Nonoxynol-4 Sulfate, Ammonium Nonoxynol-30 Sulfate, DEA-C12-13 Alkyl Sulfate, DEA-C12-15 Alkyl Sulfate, DEA-Cetyl Sulfate, DEA-C12-13 Pareth-3 Sulfate, DEA-Laureth Sulfate, DEA-Lauryl Sulfate, DEA-Myreth Sulfate, DEA-Myristyl Sulfate, Magnesium Coco-Sulfate, Magnesium Laureth-n Sulfate, where n=2, 5, 8, 16; Magnesium Lauryl Sulfate, Magnesium Myreth Sulfate, Magnesium Oleth Sulfate, Magnesium PEG-3 Cocamide Sulfate, Magnesium Sulfate, Magnesium/TEA-Coco-Sulfate, MEA-Laureth Sulfate, MEA-Lauryl Sulfate, MIPA C12-15 Pareth Sulfate, MIPA-Laureth Sulfate, MIPA-Lauryl Sulfate, Mixed Isopropanolamines Lauryl Sulfate, Potassium Glycol Sulfate, Potassium Lauryl Sulfate, Potassium Persulfate, Potassium Sulfate, Protamine Sulfate, Sodium C8-10 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium Cellulose Sulfate, Sodium Cetearyl Sulfate, Sodium Cetyl Sulfate, Sodium Cholesteryl Sulfate, Sodium Chondroitin Sulfate, Sodium Coceth Sulfate, Sodium Coceth-30 Sulfate, Sodium Coco/Babassu Sulfate, Sodium Coco/Hydrogenated Tallow Sulfate, Sodium Cocomonoglyceride Sulfate, Sodium Coco-Sulfate, Sodium C9-15 Pareth-3 Sulfate, Sodium C10-15 Pareth Sulfate, Sodium C12-13 Pareth Sulfate, Sodium C12-15 Pareth Sulfate, Sodium C13-15 Pareth-3 Sulfate, Sodium C12-14 Sec-Pareth Sulfate, Sodium Cyclodextrin Sulfate, Sodium Deceth Sulfate, Sodium Decyl Sulfate, Sodium Dermatan Sulfate, Sodium Dextran Sulfate, Sodium Dicocoylethylenediamine PEG-15 Sulfate, Sodium Ethylhexyl Sulfate, Sodium Laneth Sulfate, Sodium Laureth Sulfate, where n=2, 2, 5, 7, 8, 12, 40; Sodium Lauryl Sulfate, Sodium/MEA-PEG-3 Cocamide Sulfate, Sodium Myreth Sulfate, Sodium Myristyl Sulfate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Sulfate, Sodium Octoxynol-6 Sulfate, Sodium Octoxynol-9 Sulfate, Sodium Oleth Sulfate, Sodium Oleyl Sulfate, Sodium Stearoyl Chondroitin Sulfate, Sodium Stearyl Sulfate, Sodium Sucrose Octasulfate, Sodium Tallow Sulfate, Sodium Trideceth Sulfate, Sodium Tridecyl Sulfate, TEA-C10-15 Alkyl Sulfate, TEA-C12-13 Alkyl Sulfate, TEA-C12-14 Alkyl Sulfate, TEA-C12-15 Alkyl Sulfate, TEA-Coco-Sulfate, TEA-C12-13 Pareth-3 Sulfate, TEA-Laneth-5 Sulfate, TEA-Laureth Sulfate, TEA-Lauryl Sulfate, TEA-Oleyl Sulfate, TEA-PEG-3 Cocamide Sulfate, TIPA-Laureth Sulfate, TIPA-Lauryl Sulfate, Ammonium C9-10 Perfluoroalkylsulfonate, Ammonium Cumenesulfonate, Ammonium Dodecylbenzenesulfonate, Ammonium Xylenesulfonate, Calcium Dodecylbenzenesulfonate, Calcium Lignosulfonate, Calcium Panetheine Sulfonate, Cocamidopropyl Dimethylammonium C8-16 Isoalkylsuccinyl Lactoglobulin Sulfonate, DEA-Dodecylbenzenesulfonate, DEA-Methyl Myristate Sulfonate, Disodium Bisethylphenyl Triaminotriazine Stilbenedisulfonate, Disodium Cetyl Phenyl Ether Disulfonate, Disodium Cocoamphocarboxyethyl-hydroxypropylsulfonate, Disodium Decyl Phenyl Ether Disulfonate, Disodium Distyrylbiphenyl Disulfonate, Disodium Lauriminobishydroxypropylsulfonate, Disodium Lauryl Phenyl Ether Disulfonate, Disodium Methylene Dinaphthalenesulfonate, Isopropylamine Dodecylbenzenesulfonate, Magnesium Lauryl Hydroxypropyl Sulfonate, MIPA-Dodecylbenzenesulfonate, Potassium Cumenesulfonate, Potassium Dodecylbenzenesulfonate, Potassium Lauryl Hydroxypropyl Sulfonate, Potassium Phenylbenzimidazole Sulfonate, Potassium Toluenesulfonate, Potassium Xylene Sulfonate, Sodium Benzotriazolyl Butylphenol Sulfonate, Sodium C13-17 Alkane Sulfonate, Sodium C14-18 Alkane Sulfonate, Sodium C9-22 Alkyl Sec Sulfonate, Sodium C14-17 Alkyl Sec Sulfonate, Sodium Caproamphohydroxypropylsulfonate, Sodium Capryloamphohydroxy-propylsulfonate, Sodium Caprylyl Sulfonate, Sodium C8-16 Isoalkylsuccinyl Lactoglobulin Sulfonate, Sodium Cocoamphohydroxypropylsulfonate, Sodium Cocoglyceryl Ether Sulfonate, Sodium Cocomonoglyceride Sulfonate, Sodium C12-14 Olefin Sulfonate, Sodium C14-16 Olefin Sulfonate, Sodium C14-18 Olefin Sulfonate, Sodium C16-18 Olefin Sulfonate, Sodium C14-15 Pareth-PG Sulfonate, Sodium C12-15 Pareth-3 Sulfonate, Sodium C12-15 Pareth-7 Sulfonate, Sodium C12-15 Pareth-15 Sulfonate, Sodium Cumenesulfonate, Sodium Decylbenzenesulfonate, Sodium Dodecylbenzenesulfonate, Sodium Guaiazulene Sulfonate, Sodium Hexyldiphenyl Ether Sulfonate, Sodium Hydroxymethane Sulfonate, Sodium Lauroamphohydroxypropylsulfonate, Sodium Lignosulfonate, Sodium Methylnaphthalenesulfonate, Sodium Naphthalenesulfonate, Sodium Naphthol Sulfonate, Sodium m-Nitrobenzenesulfonate, Sodium Octoxynol-2 Ethane Sulfonate, Sodium Oleoamphohydroxypropylsulfonate, Sodium Palm Glyceride Sulfonate, Sodium Pantetheine Sulfonate, Sodium Phenolsulfonate, Sodium Phenylbenzimidazole Sulfonate, Sodium Polydimethylglycinophenolsulfonate, Sodium Polynaphthalenesulfonate, Sodium Polystyrene Sulfonate, Sodium Shale Oil Sulfonate, Sodium Stearoamphohydroxypropylsulfonate, Sodium Stearoxy PG-Hydroxyethylcellulose Sulfonate, Sodium Toluenesulfonate, Sodium Tridecylbenzenesulfonate, Sodium Xylenesulfonate, TEA-Dodecylbenzenesulfonate, TEA-Phenylbenzimidazole Sulfonate, TEA-Tridecylbenzenesulfonate, Ammonium Lauryl Sulfosuccinate, Cholesteryl C16-18 Alkenyl Succinate, Decyl Succinate, Diammonium Lauramido-MEA Sulfosuccinate, Diammonium Lauryl Sulfosuccinate, Diammonium Oleamido PEG-2 Sulfosuccinate, Diamyl Sodium Sulfosuccinate, Dicapryl Sodium Sulfosuccinate, Dicyclohexyl Sodium Sulfosuccinate, Diethoxyethyl Succinate, Diethylhexyl Sodium Sulfosuccinate, Diethylhexyl Succinate, Diethyl Succinate, Diglycol Guanidine Succinate, Diheptyl Sodium Sulfosuccinate, Disodium Cetearyl Sulfosuccinate, Disodium Cocamido MEA-Sulfosuccinate, Disodium Cocamido MIPA-Sulfosuccinate, Disodium Cocamido PEG-3 Sulfosuccinate, Disodium Coco-Glucoside Sulfosuccinate, Disodium Cocoyl Butyl Gluceth-10 Sulfosuccinate, Disodium C12-15 Pareth Sulfosuccinate, Disodium C12-14 Sec-Pareth Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Cystinyl Disuccinate, Disodium Deceth-5 Sulfosuccinate, Disodium Deceth-6 Sulfosuccinate, Disodium Dimethicone Copolyol Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Laneth-5 Sulfosuccinate, Disodium Lauramido MEA-Sulfosuccinate, Disodium Lauramido PEG-2 Sulfosuccinate, Disodium Lauramido PEG-5 Sulfosuccinate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleth-3 Sulfosuccinate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-5 Laurylcitrate Sulfosuccinate, Disodium PEG-8 Palm Glycerides Sulfosuccinate, Disodium PEG-8 Ricinosuccinate, Disodium Ricinoleamido MEA-Sulfosuccinate, Disodium Sitostereth-14 Sulfosuccinate, Disodium Stearamido MEA-Sulfosuccinate, Disodium Stearyl Sulfosuccinate, Disodium Succinate, Disodium Tallamido MEA-Sulfosuccinate, Disodium Tallowamido MEA-Sulfosuccinate, Disodium Tetrapropenyl Succinate, Disodium Tridecylsulfosuccinate, Disodium Undecylenamido MEA-Sulfosuccinate, Disodium Undecylenamido PEG-2 Sulfosuccinate, Disodium Wheat Germamido MEA-Sulfosuccinate, Disodium Wheat Germamido PEG-2 Sulfosuccinate, Di-TEA-Oleamido PEG-2 Sulfosuccinate, Glyceryl Stearate Succinate, Hydroxypropyl Methylcellulose Acetate/Succinate, Isostearyl Diglyceryl Succinate, Methoxy-PEG-7 Rutinyl Succinate, PEG-20 Hexadecenylsuccinate, PEG-50 Hydrogenated Castor Oil Succinate, PEG-3 PPG-20 Succinate, Potassium Dextrin Octenylsuccinate, Potassium PEG-50 Hydrogenated Castor Oil Succinate, Sodium Bisglycol Ricinosulfosuccinate, Sodium Dextrin Octenylsuccinate, Sodium/MEA Laureth-2 Sulfosuccinate, Sodium PEG-50 Hydrogenated Castor Oil Succinate, Sodium Starch Octenylsuccinate, TEA-Dextrin Octenylsuccinate, TEA-PEG-50 Hydrogenated Castor Oil Succinate.

Ammonium Laureth-6 Carboxylate, Ammonium Laureth-8 Carboxylate, Cetyl C12-15-Pareth-9 Carboxylate, Cetyl PPG-2 Isodeceth-7 Carboxylate, Isopropyl C12-15-Pareth-9 Carboxylate, Isopropyl PPG-2-Isodeceth-7 Carboxylate, Magnesium Laureth-11 Carboxylate, MEA-Laureth-6 Carboxylate, MEA PPG-6 Laureth-7 Carboxylate, MEA-PPG-8-Steareth-7 Carboxylate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Trideceth-n, where n=3, 3, 7, 15, 19, Sodium Capryleth-2 Carboxylate, Sodium Capryleth-9 Carboxylate, Sodium Ceteth-13 Carboxylate, Sodium C9-11 Pareth-6 Carboxylate, Sodium C11-15 Pareth-7 Carboxylate, Sodium C12-13 Pareth-n Carboxylate, where n=6, 8, 12, Sodium C12-15 Pareth-n Carboxylate, where n=6, 7, 8, Sodium C14-15 Pareth-8 Carboxylate, Sodium C12-14 Sec-Pareth-8 Carboxylate, Sodium Isosteareth-6 Carboxylate, Sodium Isosteareth-11 Carboxylate, Sodium Laureth-3 Carboxylate, Sodium Laureth-n Carboxylate, where n=4, 5, 6, 8, 11, 12, 13, 14, 17, Sodium Lauryl Glycol Carboxylate, Sodium PEG-6 Cocamide Carboxylate, Sodium PEG-8 Cocamide Carboxylate, Sodium PEG-3 Lauramide Carboxylate, Sodium PEG-4 Lauramide Carboxylate, Sodium PEG-7 Olive Oil Carboxylate, Sodium PEG-8 Palm Glycerides Carboxylate, Sodium Trideceth-3 Carboxylate, where n=3, 4, 6, 7, 8, 12, 15, 19, Sodium Undeceth-5 Carboxylate.

Ammonium Cocoyl Sarcosinate, Ammonium Lauroyl Sarcosinate, Isopropyl Lauroyl Sarcosinate, Potassium Cocoyl Sarcosinate, Potassium Lauroyl Sarcosinate, Sodium Cocoyl Sarcosinate, Sodium Lauroyl Sarcosinate, Sodium Myristoyl Sarcosinate, Sodium Palmitoyl Sarcosinate, TEA-Cocoyl Sarcosinate, TEA-Lauroyl Sarcosinate, TEA-Oleoyl Sarcosinate, TEA-Palm Kernel Sarcosinate, Palmitoyl Oligopeptide, Pantothenic Acid Polypeptide, Ammonium Cocoyl Isethionate, Dibromopropamidine Diisethionate, Hexamidine Diisethionate, Sodium Cocoyl Isethionate, Sodium Isethionate, Sodium Lauroyl Isethionate, Sodium Myristoyl Isethionate, Sodium Oleoyl Isethionate.

Aluminum Dicetyl Phosphate, Benzalkonium Cetyl Phosphate, C8-10 Alkyl Ethyl Phosphate, C9-15 Alkyl Phosphate, Ceteareth-2 Phosphate, Ceteareth-4 Phosphate, Ceteareth-5 Phosphate, Ceteareth-10 Phosphate, Ceteth-8 Phosphate, Ceteth-10 Phosphate, Cetyl Phosphate, Cocamidopropyl PG-Dimonium Chloride Phosphate, Cocoyl Hydroxyethylimidazolinium PG-Chloride Phosphate, C6-10 Pareth-4 Phosphate, C12-13 Pareth-10 Phosphate, C12-15 Pareth-n Phosphate, where n=2, 3, 6, 8, 9, 10; C12-16 Pareth-6 Phosphate, DEA-Ceteareth-2 Phosphate, DEA-Cetyl Phosphate, DEA-C8-18 Perfluoroalkylethyl Phosphate, DEA-Oleth-3 Phosphate, DEA-Oleth-n Phosphate, where n=5, 10, 20; DEA-Polyperfluoroethoxymethoxy PEG-2 Phosphate, Deceth-9 Phosphate, Deceth-4 Phosphate, Deceth-6 Phosphate, Diceteareth-10 Phosphate, Dicetyl Phosphate, Di-C12-15 Pareth-n Phosphate, where n=2, 4, 6, 8, 10; Dilaureth-4 Phosphate, Dilaureth-10 Phosphate, Dimyristyl Phosphate, Dioleth-8 Phosphate, Disodium Lauryl Phosphate, Disodium Oleyl Phosphate, Glycereth-26 Phosphate, Hydrogenated Vegetable Glycerides Phosphate, Hydroxyethyl Cetyldimonium Phosphate, Isosteareth-2 Phosphate, Laneth-4 Phosphate, Laureth-n Phosphate, where n=1, 2, 3, 4, 7, 8; Lauryl Phosphate, Linoleamidopropyl PG-Dimonium Chloride Phosphate, Manganese Glycerophosphate, MEA-Dicetearyl Phosphate, Myristamidopropyl Dimethylamine Dimethicone Copolyol Phosphate, Myristamidopropyl Dimethylamine Phosphate, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-n Phosphate, where n=7, 8, 9, 10, 11, 15, 24, Oleth-n Phosphate, where n=2, 3, 4, 5, 10, 20, Oleyl Ethyl Phosphate, Oleyl Phosphate, Palmeth-2 Phosphate, PEG-15 Cocamine Oleate/Phosphate, PEG-26-PPG-30 Phosphate, PEG-45 Stearate Phosphate, Potassium C9-15 Alkyl Phosphate, Potassium C12-13 Alkyl Phosphate, Potassium Cetyl Phosphate, Potassium Deceth-4 Phosphate, Potassium Dihydroxyethyl Cocamine Oxide Phosphate, Potassium Dimethicone Copolyol Panthenyl Phosphate, Potassium Dimethicone Copolyol Phosphate, Potassium Glycerophosphate, Potassium Isosteareth-2 Phosphate, Potassium Lauryl Phosphate, Potassium Monofluorophosphate, Potassium Trideceth-6 Phosphate, PPG-21 Butyl Ether Phosphate, PPG-25 Butyl Ether Phosphate, PPG-35 Butyl Ether Phosphate, PPG-5-Ceteth-10 Phosphate, PPG-10 Cetyl Ether Phosphate, Sodium Coco PG-Dimonium Chloride Phosphate, Sodium C13-15 Pareth-8 Butyl Phosphate, Sodium C13-15 Pareth-8 Phosphate, Sodium Diceteareth-10 Phosphate, Sodium Dihydroxycetyl Phosphate, Sodium Dilaureth-10 Phosphate, Sodium Dioleth-8 Phosphate, Sodium Emuamidopropyl PG-Dimonium Chloride Phosphate, Sodium Glyceryl Oleate Phosphate, Sodium Laureth-4 Phosphate, Sodium Lauroampho PG-Acetate Phosphate, Sodium Lauryl Phosphate, Sodium Milkamidopropyl PG-Dimonium Chloride Phosphate, Sodium Monofluorophosphate, Sodium Oleamidopropyl PG-Dimonium Chloride Phosphate, Sodium Oleth-7 Phosphate, Sodium Oleth-8 Phosphate, Sodium Olivamidopropyl PG-Dimonium Chloride Phosphate, Sodium Steareth-4 Phosphate, Sodium Sunfloweramidopropyl PG-Dimonium Chloride Phosphate, Sodium Zinc Cetyl Phosphate, Stearamidoethyl Diethylamine Phosphate, Stearamidoethyl Ethanolamine Phosphate, Stearamidopropyl PG-Dimonium Chloride Phosphate, Steardimonium Hydroxypropyl PEG-7 Dimethicone Phosphate, Steareth-2 Phosphate, Steareth-3 Phosphate, Stearyl PG-Dimonium Chloride Phosphate, Stearyl Phosphate, TEA-C12-13 Alkyl Phosphate, TEA-Dimethicone Copolyol Phosphate, TEA-Polyphosphatel Triceteareth-4 Phosphate, Triceteth-5 Phosphate, Tricetyl Phosphate, Tri-C12-15 Pareth-n Phosphate, where n=2, 6, 8, 10, Tricresyl Phosphate, Trideceth-n Phosphate, where n=3, 6, 10, Trilaureth-4 Phosphate, Trilauryl Phosphate, Trioleth-8 Phosphate, Trioleyl Phosphate, Trisodium Lauroampho PG-Acetate Chloride Phosphate, Tristearyl Phosphate.

Non-limiting examples of amphoteric surfactants which may be employed as emulsifiers include: Almondamido-propyl Betaine, Apricotamidopropyl Betaine, Avocadamidopropyl Betaine, Babassuamidopropyl Betaine, Behenamidopropyl Betaine, Behenyl Betaine, Canolamidopropyl Betaine, Capryl/Capramidopropyl Betaine, Cetyl Betaine, Cocamidoethyl Betaine, Cocamidopropyl Betaine, Coco-Betaine, Coco/Oleamidopropyl Betaine, Decyl Betaine, Hydrogenated Tallow Betaine, Isostearamidopropyl Betainem Lauramidopropyl Betaine, Lauryl Betaine, Milkamidopropyl Betaine, Minkamidopropyl Betaine, Myristamidopropyl Betaine, Myristyl Betainem Oleamidopropyl Betaine, Oleyl Betaine, Olivamidopropyl Betaine, Palmamidopropyl Betaine, Palmitamidopropyl Betaine, Palm Kernelamidopropyl Betaine, Polytetrafluoroethylene Acetoxypropyl Betaine, Ricinoleamidopropyl Betaine, Sesamidopropyl Betaine, Soyamidopropyl Betaine, Stearamidopropyl Betaine, Stearyl Betaine, Tallowamidopropyl Betaine, Tallow Betaine, Tallow Dihydroxyethyl Betaine, Undecylenamidopropyl Betaine, Wheat Germamidopropyl Betaine, Almondamidopropylamine Oxide, Babassuamidopropylamine Oxide, Behenamine Oxide, Cocamidopropylamine Oxide, Cocamine Oxide, Decylamine Oxide, Decyltetradecylamine Oxide, Diaminopyrimidine Oxide, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Hydrogenated Palm Kernel Amine Oxide, Hydrogenated Tallowamine Oxide, Hydroxyethyl Hydroxypropyl C12-15 Alkoxypropylamine Oxide, Isostearamidopropylamine Oxide, Isostearamidopropyl Morpholine Oxide, Lauramidopropylamine Oxide, Lauramine Oxide, Laurtrimonium Trichlorophenoxide, Milkamidopropyl Amine Oxide, Minkamidopropylamine Oxide, Myristamidopropylamine Oxide, Myristamine Oxide, Myristyl/Cetyl Amine Oxide, Oleamidopropylamine Oxide, Oleamine Oxide, Olivamidopropylamine Oxide, Palmitamidopropylamine Oxide, PPalmitamine Oxide, PEG-3 Lauramine Oxide, Sesamidopropylamine Oxide, Soyamidopropylamine Oxide, Stearamidopropylamine Oxide, Stearamine Oxide, Tallowamidopropylamine Oxide, Tallowamine Oxide, Wheat Germamidopropylamine Oxide.

The chemical formulation may also comprise one or more emulsifiers, including, but not limited to, non-ionic emulsifiers, anionic emulsifier and amphoteric emulsifiers.

In another embodiment of the present invention, the chemical formulation comprises a siloxane in a concentration range of about 3% to 100% siloxane, preferably about 10% to 75% siloxane, more preferably about 17.5% to 40% siloxane, wherein the resulting liquid formulation has a surface tension below 25 dynes/cm at 20° C. and a viscosity above 200 cst. In accordance with yet another embodiment of the present invention, there is provided a chemical formulation comprising a combination of two or more siloxanes wherein the resulting total siloxane concentration range is about 3% to 100% siloxane, preferably about 10% to 75% siloxane, more preferably about 17.5% to 40% siloxane, wherein the resulting liquid formulation has a surface tension below 25 dynes/cm at 20° C. and a viscosity above 200 cst.

The chemical formulations of the present invention can be used to treat body infestations of lice, nits, fleas, ticks and the like. The chemical formulations of the present invention can be applied to an insect infestation for a sufficient period of time to achieve at least 60% insect mortality, preferably 85% insect mortality, more preferably 100% insect mortality.

In an embodiment of the present invention there is provided a method of treatment of a body insect infestation comprising topically applying a chemical formulation as described herein to a subject in need thereof and allowing the formulation to remain on the insect infestation for at least 5 minutes, preferably about 30 minutes to 1 hour, more preferably about 1 hour to 8 hours.

The chemical formulations of the present invention may further comprise chemical additives, such as alcohols or water, which rapidly evaporate, usually within fifteen to twenty minutes, when left of the hair of the subject such that the resulting total concentration of siloxane following evaporation of the additives is at least 3% by volume.

In order to illustrate the efficacy of the present invention the following test examples are presented.

Example 1

Two tests were conducted using a compound containing 60% silicone-based oil. In the first test the compound was placed on a louse on a paper towel. After 5 minutes, the louse washed off with Prell® shampoo and water. The louse was observed one minute later and was dead. In the second test using the same compound, the compound was applied to the long, thick hair of a school girl, which had been infested with lice for several months. After five minutes, the compound was removed by several washes with Prell® shampoo, with the compound being otherwise difficult to extract from the hair. The infestation was successfully treated and no lice or nits returned.

Example 2

Additional tests were conducted using a 100% concentration of Dow corning Fluid Food Grade silicone (350 CST) (the "silicone"). These tests also revealed that, in addition to killing lice, the silicone was effective at preventing nits from maturing. In these tests, silicone was applied directly to head lice, body lice, and to the hair of several children infested with head lice.

In the first Silicone experiment, three head lice were collected from school children. The lice were placed on the hand of a subject and they attached themselves to the hair on the subject's hand. After five minutes, the lice were gently washed off with Prell® shampoo and then water.

Although there appeared to be mortality within minutes, the lice were left on the hand for further examination (they were covered with a loosely fitting bandage to make sure they did not fall off). During the following six hours, the lice were checked periodically and all were found to be dead.

Example 3

In a further Silicone experiment, Silicone was directly applied to the hair of three school children, each of which had been infested with lice and nits. Each of the children applied the silicone directly to his or her hair and left it on for five minutes. After five minutes, the hair was washed first with Prell® shampoo and then with Johnson's Baby Shampoo®. In all three cases the infestation was successfully ended with one application.

In a continuing experiment, Silicone was directly applied to the hair of twenty school children, each of which had been infested with lice and nits. Each of the children applied the silicone directly to his or her hair and left it on for ten minutes. After ten minutes, the hair was washed with a shampoo of the parent's choice. In all twenty cases the infestation was successfully ended with one application.

Example 4

In another experiment ten adult lice were immersed in the Silicone for ten minutes, then washed and rinsed for one minute each in water. A set of ten control lice were immersed in water for ten minutes and then also washed and rinsed for one minute. The lice were then held in an incubator. A review of the lice after one hour, and again after twenty-four hours, revealed a 100% morality of those who had been immersed in Silicone. There was no morality among the controls.

Example 5

In an additional experiment, ten adult lice were immersed in the Silicone for ten minutes, and subsequently washed in a dilution of 50:50 Johnson's Baby Shampoo® and tap water. To test the effectiveness at different concentrations of Silicone, four mixtures were made using the Silicone with Johnson's Baby Shampoo® with the following concentrations:
 (a) 100% Johnson's Baby Shampoo
 (b) 3% Silicone and 97% Johnson's Baby Shampoo
 (c) 15% Silicone and 85% Johnson's Baby Shampoo
 (d) 40% Silicone and 60% Johnson's Baby Shampoo
 (e) Control with water The results of the test after 24 hours were that for samples (a) and (c), one louse was dead; for samples (b) and (e), no lice were dead. The one louse being dead was considered not statistically significant. In sample (d), containing 40% Silicone, four lice were dead, indicating that at this concentration there is some effectiveness of the Silicone in killing lice but not a fully useful concentration. It is believed that other ingredients may interfere with the effectiveness of the Silicone, and accordingly it is preferred to use the Silicone in a high concentration or in a pure state.

Example 6

In another experiment to determine the effect of lubricants of various surface tensions, a test was done using 10 adult lice immersing them into one of three solutions for ten minutes and then washing them of with a soapy water solution. The three lubricants used were: (1) Johnson's baby oil, a mineral oil; (2) Ultra pure lamp oil, 99% pure liquid paraffin; and (3) Krytox® 1514 Vacuum pump fluid, produced by Dupont®. The lice were then observed after one hour, and three hours and the amount dead were the same at both intervals in all tests. The mortality rate was highest for the Krytox® 1514 with nine of ten dead within one hour, lowest for the liquid paraffin with three of ten dead within one hour, and moderate for the mineral oil with four of ten dead within one hour. In a repeat of the experiment for the Krytox, seven out of ten where dead within one hour, for liquid paraffin two out of ten, and for mineral oil five out of ten.

The preferred embodiment for use as a head lice treatment is to use the Silicone in its pure state, that is Dow Corning 200 fluid, 350 CST, which is a silicone fluid termed dimethylpolysiloxane. The Silicone is water white and has a consistency of light syrup. This form is preferred as it clings easily to the hair. The Silicone is applied to the entire head, left on for at least ten minutes, and then washed off with any standard shampoo. Within a short time after application of the shampoo, the area is free of any live lice. Any nits that remain do not mature.

Other embodiments include the processing of synthetic lubricants into a shampoo that effectively kills ticks, fleas, and other insects. The concentration of such lubricants, and the amount of time they must remain on the affected area, is above 50% by volume and is adjusted depending on the type of insect being treated. Thus, for example, in two experiments conducted on ticks, the ticks took longer to die than the lice did in the prior experiments using pure Silicone treatment. In the first tick experiment, ten *Amblyomma Americanum* ticks were coated with Silicone, and ten were coated with Prell® Shampoo. After ten minutes, both sets of ticks were washed with water and Prell® Shampoo for five minutes, until all of the Silicone and shampoo were removed. While all of the "Silicone" ticks were alive after one hour, after six hours three of the ticks were dead, five were morbid, and two were alive. After twenty-four hours, all of the "Silicone" ticks were dead, whereas only two of the "Prell®" ticks were dead.

In a second tick experiment, ten *Dermacentor Varibilis* ticks were coated with Silicone. After ten minutes all of the ticks were still alive. After ninety minutes, all of the ticks were dead.

While Silicone has been used for many years as a hair-bodying agent, and there are many patents (U.S. Pat. No. 3,964,500, U.S. Pat. No. 4,427,557, U.S. Pat. No. 4,465,619, U.S. Pat. No. 4,704,272, U.S. Pat. No. 5,728,457, U.S. Pat. No. 4,749,732, U.S. Pat. No. 4,842,850. U.S. Pat. No. 5,015,415, U.S. Pat. No. 5,034,218, U.S. Pat. No. 5,063,044. U.S. Pat. No. 4,902,499, U.S. Pat. No. 4,906,459, U.S. Pat. No. 5,554,313, U.S. Pat. No. 577,644) that focus on using silicone, and some specifically polysiloxanes, for various benefits to the hair. Such use levels have always been at concentrations below 50% wherein effectiveness for insect control was not evident. For actual effectiveness use in the range of 50-100% concentration is required.

It is believed that the lubricating properties of the silicone provide a morbidity passageway for interfering with insect respiratory and possibly digestive functions, and accordingly other similar lubricants and Silicone derivatives are effective in such insect control.

With regard to head lice, the point of entry where the silicone permeates the head lice is very likely the thoracic spiracle, the honeycomb structure which creates maximum surface area and efficient exchange of air and moisture. The nits are likely affected via the head louse nit operculum which contain doughnut shaped holes. See Meinking, T. L. 11 (3) pp 73-120 May/June 1999.

With regard to head lice many natural oils treatments have been attempted but with limited efficacy. In a school-based study to evaluate alternative treatments, children with head lice were treated with olive oil, mayonnaise, or Vasoline® petroleum jelly overnight under a shower cap. They came to school the next day with their greasy hair still covered by shower caps. After a shampoo rinse the lice from heads treated with olive oil or mayonnaise were found to still be alive. The children who used Vasoline® had many dead nymphs stuck to the scalp or hair but some adult lice were still alive. See Meinking, T. L., ibid.

The efficacy of silicone-based lubricants over other oils appears to be related to the lubricity of silicone. Silicone and more particularly dimethylpolysiloxane (or polydimethylsiloxane) has a far lower surface tension than other oils. Surface tension is a measure of the stretching force required to form a liquid film, and is equal to the surface energy of the liquid per unit length of the film at equilibrium; the force tends to minimize the area of a surface. Surface tension is caused by the attraction of molecules to each other.

Below is a list of the surface tensions of a variety of polymers and oils at 20° C.

TABLE 1

| Polymer/Oil System | Surface Tension (dynes/cm) |
| --- | --- |
| Polydimethylsiloxane (PDMS) | 20.9[1] |
| Polyisobutylene (PIB) | 35.6[1] |
| n-alkanes | 37.8[1] |
| n-fluoroalkanes | 25.9[1] |
| Diesel fuel | 25[2] |
| Deodorized sunflower oil | 33[2] |
| Crude soybean oil | 32[2] |
| Refined soybean oil | 32[2] |
| Cottonseed oil | 35.4[3] |
| Coconut oil | 33.4[3] |
| Olive oil | 33.0[3] |
| Corn oil | 33.4[4] |
| Peanut oil | 35.5[4] |
| Mineral oil (MWP paraffin) | 28.8[4] |
| Mineral oil - baby oil | 30.8[5] |
| Liquid paraffin | 26-28[5] |
| Krytox 1514 | 18[6] |

[1]Rayan, T. W.; Callahan. T. J.; and Dodge, L. G. in Vegetable Oil Fuels, ASAE Conference, 1982 pg. 72
[2]Clarson, S. and Semlyem, J. A. in Siloxane Polymers, PTR Prentice Hall, 1993 pp. 323-325
[3]Encyclopedia of Food Science and Technology, Hui, Y. H. editor Volume 4, pg. 2449 John Wiley and Sons, 1992
[4]Kirk-Othmer Encyclopedia of Chemical Technology, Fourth Edition, Kroschwitz, J. I. and Howe-Grant, M. editors volume 7 pg. 936 John Wiley and Sons, 1992
[5]Internal study by Penrico, courtesy Harold Faust.
[6]Technical data sheet, Dupont.

The surface tension of polydimethylsiloxane at about 20.9 dynes/cm is about 50% lower than the surface tension of most natural oils and is believed to account for its greater ability to penetrate and induce morbidity in insects. In the experiment with Krytox® 1514 a fluorinated oil PerFluoroPolyEther (PFPE), with a surface tension of 18, it was determined that it was also effective in killing lice but slightly less effective than Dow Corning 200 fluid, 350 CST. The greater effectiveness of the Dow Corning 350 CST material is very likely due to its greater viscosity. Viscosity, or kinematic viscosity is measured in stokes, and is defined to be the dynamic viscosity divided by the density of the liquid; this gives a quantity which depends only on the type of the liquid, independent of its concentration or density. Krytox 1514 has a viscosity of 142 centistokes (cst) while Dow Corning 200 fluid, 350 CST has a viscosity of 350 cst. The viscosity adds to the effectiveness by creating better adhesion of the lubricant to the insects.

Attempts have been made to modify vegetable oils thru processes such as transesterification in order to lower their surface tensions and thus make them usable as biodiesel fuels. See Cecil, A. W.; Allen, K.; Watts, C. and Adman R. G. in "Predicting the Surface Tension of Biodiesel Fuels from Their Fatty Acid Composition". JAOCS 76(3), pp. 317-323 (March 1999). It is probable that if vegetable or other oils were processed to lower their surface tension close to the surface tension found in polydimethylsiloxane, i.e. less than about 25 dynes/centimeter, it would have the same effect on the lice.

Example 7

The following formulations were tested for efficacy in killing lice. All of the formulations have a surface tension below 25 dynes/cm at 20° C. These formulations are manufactured by Chemsil Silicones, Inc. Methods of formulating the formulations of Table 2 are described in U.S. Pat. No. 6,605,577, incorporated herein by reference.

TABLE 2

| Formulation Components | Trade Name | Viscosity (cst) |
| --- | --- | --- |
| Propoxytetramethyl piperidinyl dimethicone and C-11 Pareth-7 and Trideceth-6 (base fluid is 90,000 cst) | MICROSIL HAF-HV | 500 |
| Propoxytetramethyl piperidinyl dimethicone and C-11 Pareth-7 and Trideceth-6 (base fluid is 10,000 cst) | MICROSIL HAF-MV-30 | 500 |
| Cyclomethicone and dimethicone | COSMETIC FLUID 9005-DM | 500 |
| Cyclopentasiloxane and dimethicone | COSMETIC FLUID 4306-DM | 300 |

The test formulations listed in Table 2 were tested against a plain water control. Approximately ten lice were submerged in the test formulation for ten minutes. They were then washed with mild soap and water. After ten minutes all of the lice in the test formulations were found to be morbid or moribund. After 24 hours all of the lice were dead. The lice in the control group were all alive after 24 hours.

It should be noted that any siloxane that has a surface tension below 25 dynes/cm at 20° C. and a viscosity above 200 cst will be efficacious in the killing of lice, nits and other infestational insects, such as fleas and ticks, for use alone or as part of a formulation, so long as the final liquid formulation has a surface tension below 25 dynes/cm at 20° C. and a viscosity above 200 cst. Non-limiting examples of suitable siloxanes which may be utilized in the chemical formulation are listed in Table 3.

TABLE 3

| INCI[1] Name | Chemical/IUPAC[2] Name | CAS No. |
| --- | --- | --- |
| ACRYLATES/DEMETHIONE COPOLYMER | Polydimethylsiloxane, copolymer with one or more monomers of acrylic acid, methacrylic acid or one of their simple esters | |
| AMINO BISPROPYL DIMETHICONE | 1,1'-iminobis(3-(tris(trimethylsiloxy)silyl)propane | |
| AMINO BISPROPYL DIMETHICONE | | 243842-22-0 |
| AMMONIUM DIMETHICONE COPOLYOL SULFATE | Dimethylsiloxane, polymer, mono(15-hydroxy-1,3-dimethyl-1-(3-(2-(2-(2-(fulfooxy)ethoxy)ethoxy)ethoxy)propyl)-3-((trimethylsilyl)oxy)-2,7,10,13-tetraoxa-1,3- | 130381-11-2 |

TABLE 3-continued

| INCI[1] Name | Chemical/IUPAC[2] Name | CAS No. |
|---|---|---|
| | disilapentadec-1-yl)oxy)-terminated, ammonium salts | |
| AMODIMETHICONE | Dimethylsiloxane, polymer, (((3-((2-aminoethyl)amino)propyl)-diethoxysilyl)oxy)-terminated | 71750-80-6 |
| AMODIMETHICONE HYDROXY STEARATE | 3-(2-Aminoethylamino)propylsilane, polymer with dimethylsiloxane, 12-hydroxyoctadecanoates | |
| AMODIMETHICONE/DIMETHICONE COPOLYOL | 3-(2-Aminoethylamino)propylsilane, polymer with dimethylsiloxane, ethoxylated, propoxylated | |
| BEHENOXY DIMETHICONE | Poly(oxy(diemthylsilylene)), α-docosyl-ω-(docosyloxy)- | 193892-43-2 |
| BISPHENYLHEXAMETHICONE | Tetrasiloxane, 1,1,1,7,7,7-hexamethyl-3,5-diphenyl-3,5-bis[(trimethylsilyl)oxy]- | 18758-91-3 |
| C24-28 ALKYL METHICONE | Siloxanes and silicones, C24-28-alkyl methyl | 158061-44-0 |
| C30-45 ALKYL DIMETHICONE | Poly[oxy(dimethylsilylene)], α-(C30-45)-alkyldimethylsilyl-ω-(C30-45)-alkyloxy | |
| C30-45 AKLYL METHICONE | Siloxanes and silicones, C30-45-alkyl methyl | 246864-88-0 |
| CETEARYL DIMETHICONE/VINYL DIMETHICONE CROSSPOLYMER | Siloxanes and silicones, dimethyl, methyl vinyl, polymers with mono-(C16-18-alkoxy)-terminated dimethyl siloxanes | 243137-50-0 |
| CETEARYL METHICONE | Poly{oxy[(C16-18)-alkylmethylsilylene]}, trimethylsilyl terminated | 227200-32-0 |
| CETYL CAPRYLATE | Hexadecyl octanoate | 29710-31-4 |
| CETYL DIMETHICONE | Siloxanes and silicones, hexadecyl methyl, demethyl | 191044-49-2 |
| CETYL DIMETHICONE COPOLYOL | Siloxanes and silicones, hexadecyl methyl, dimethyl, polymers with ethoxylated propoxylated dimethyl siloxanes | 251320-26-0 |
| CETYL TRIETHYLAMMONIUM DIMETHICONE COPOLYOL PHTHALATE | Dimethylpolysiloxane, ethoxylated, propoxylated, 2-carboxybenzoate esters, hexadecyltrimethylammonium salts | |
| CYCLOETHOXYMETHICONE | Methylethoxysiloxane cyclic polymer | |
| CYCLOHEXASILOXANE | Dodecamethylcyclohexasiloxane | 540-97-6 |
| CYCLOMETHICONE | Octamethylcyclotetrasiloxane | 556-67-2 |
| CYCLOPENTASILOXANE | Decamethylcyclopentasiloxane | 541-02-6 |
| CYCLOTETRASILOXANE | Octamethylcyclotetrasiloxane | 556-67-2 |
| CYCLCOTRISILOXANE | Hexamethylcyclotrisiloxane | 541-05-9 |
| DIAMMONIUM DIMETHICONE COPOLYOL SULFOSUCCINATE | | |
| DIISOSTEAROYL TRIMETHYLOLPROPANE SILOXY SILICATE | | |
| DILAUROYL TRIMETHYLOLPROPANE SILOXY SILICATE | | |
| DILINOLEAMIDOPROPYL DIMETHYLAMINE DIMETHICONE COPOLYOL PHOSPHATE | | 138698-34-7 |
| DIMETHICONE | Dimethicone | 9006-65-9/631 |
| DIMETHICONE BISAMINOHYDROXYPROPYL COPOLYOL | Siloxanes and silicones, dimethyl, 3-(3-amino-2-hydroxypropoxy)propyl group terminated, ethoxylated propoxylated | 244058-69-3 |
| DIMETHICONE COPOLYOL | Siloxanes and silicones, di-Me, hydroxy-terminated, ethoxylated propoxylated | 64365-23-7 |
| DIMETHICONE COPOLYOL ACETATE | | |
| DIMETHICONE COPOLYOL ADIPATE | | |
| DIMETHICONE COPOLYOL ALMONDATE | | |
| DIMETHICONE COPOLYOL AVOCADOATE | | |
| DIMETHICONE COPOLYOL BEESWAX | | |
| DIMETHICONE COPOLYOL BEHENATE | | |
| DIMETHICONE COPOLYOL BENZOATE | Ester of dimethylsiloxane-glycol copolymer and benzoic acid | |
| DIMETHICONE COPOLYOL | Siloxanes and silicones, 3-[3-bis(2- | 244058- |

TABLE 3-continued

| INCI[1] Name | Chemical/IUPAC[2] Name | CAS No. |
|---|---|---|
| BISHYDROXYETHYLAMINE | hydroxyethyl)amino]-2-hydroxypropoxy]propy methyl, dimethyl, 3-hydroxylpropoxy methyl, ethoxylated propoxylated | 65-9 |
| DIMETHICONE COPOLYOL BORAGEATE | Ester of dimethylsiloxane-glycol copolymer and the fatty acid derived from Borago officinalis seed oil | |
| DIMETHICONE COPOLYOL BUTYL ETHER | | |
| DIMETHICONE COPOLYOL COCOA BUTTERATE | | |
| DIMETHICONE COPOLYOL CROSSPOLYMER | Crosspolymer of dimethylsiloxane-glycol copolymer crosslinked with a polyethylene glycol diallyl ether | |
| DIMETHICONE COPOLYOL DHUPA BUTTERATE | Ester of dimethylsiloxane-glycol copolymer and the fatty acids derived from Dhupa butter | |
| DIMETHICONE COPOLYOL HYDROXYSTEARATE | | |
| DIMETHICONE COPOLYOL ISOSTEARATE | | |
| DIMETHICONE COPOLYOL KOKUM BUTTERATE | Ester of dimethylsiloxane-glycol copolymer and the fatty acids derived from Kokum butter | |
| DIMETHICONE COPOLYOL LAURATE | | |
| DIMETHICONE COPOLYOL MANGO BUTTERATE | Ester of dimethylsiloxane-glycol copolymer and the fatty acids derived from Mango butter | |
| DIMETHICONE COPOLYOL METHYL ETHER | | 68951-97-3 |
| DIMETHICONE COPOLYOL MOHWA BUTTERATE | Ester of dimethylsiloxane-glycol copolymer and the fatty acids derived from Mohwa butter | |
| DIMETHICONE COPOLYOL OCTYLDODECYL CITRATE | Mixed ester of citric acid and dimethylsiloxane-glycol copolymer and 2-octyl-1-dodecanol | |
| DIMETHICONE COPOLYOL OLIVATE | | |
| DIMETHICONE COPOLYOL PHOSPHATE | | |
| DIMETHICONE COPOLYOL PHTHALATE | | |
| DIMETHICONE COPOLYOL SAL BUTTERATE | Ester of dimethylsiloxane-glycol copolymer and the fatty acids derived from Sal butter | |
| DIMETHICONE COPOLYOL SHEA BUTTERATE | | |
| DIMETHICONE COPOLYOL STEARATE | | |
| DIMETHICONE COPOLYOLAMINE | | 133779-14-3 |
| DIMETHICONE HYDROXYPROPYL TRIMONIUM CHLORIDE | Siloxanes and silicones, dimethyl, 3-[2-hydroxy-3-(trimethylammonio)propoxy]propyl methyl, chlorides | 133779-10-9 |
| DIMETHICONE PROPYL PG-BETAINE | | |
| DIMETHICONE PROPYLETHYLENEDIAMINE BEHENATE | | 132207-30-8 |
| DIMETHICONE SILYLATE | | |
| DIMETHICONE/MERCAPTOPROPYL METHICONE COPOLYMER | | |
| DIMETHICONE/PHENYL VINYL DIMETHICONE CROSSPOLYMER | Siloxanes and silicones, dimethyl, polymers with [(dimethylphenylsilyl)oxy]- and [(ethenyldimethylsilyl)oxy]-terminated dimethyl siloxanes | 243137-51-1 |
| DIMETHICONE/SODIUM PG PROPYLDIMETHICONE THIOSULFATE COPOLYMER | | |
| DIMETHICONE/VINYL DIMETHICONE CROSSPOLYMER | Siloxanes and silicones, dimethyl, polymers with [(ethenyldimethylsilyl)oxy]-terminated dimethyl siloxanes | 243137-53-3 |
| DIMETHICONOL | Poly[oxy(dimethylsilylene)], α-hydro-ω-hydroxy- | 31692-79-2 |
| DIMETHICONOL BEESWAX | Reaction product of beeswax and poly[oxy(dimethylsilylene)], α-hydro-ω-hydroxy | 227200-35-3 |

TABLE 3-continued

| INCI[1] Name | Chemical/IUPAC[2] Name | CAS No. |
|---|---|---|
| DIMETHICONOL BEHENATE | Reaction product of docosanoic acid and poly[oxy(dimethylsilylene)], α-hydro-ω-hydroxy | 227200-34-2 |
| DIMETHICONOL BORAGEATE | Reaction product of the fatty acids derived from Borago officinalis seed oil and poly[oxy(dimethylsilylene)], α-hydro-ω-hydroxy | 226994-45-2 |
| DIMETHICONOL DHUPA BUTTERATE | Silicones and siloxanes, dimethyl, hydroxy-terminated, esters with Vateria indica fatty acids | 243981-39-7 |
| DIMETHICONOL FLUOROALCOHOL DILINOLEIC ACID | | |
| DIMETHICONOL HYDROXYSTEARATE | | |
| DIMETHICONOL ILLIPE BUTTERATE | Reaction product of the fatty acids derived from Illipe (Bassia latifolia) butter and poly[oxy(dimethylsilylene)], α-hydro-ω-hydroxy | |
| DIMETHICONOL ISOSTEARATE | | |
| DIMETHICONOL KOKUM BUTTERATE | Reaction product of the fatty acids derived from Kokum butter and poly[oxy(dimethylsilylene)], α-hydro-ω-hydroxy | 226994-48-5 |
| DIMETHICONOL LACTATE | Silicones and siloxanes, dimethyl, hydroxy-terminated, 2-hydroxypropanoates | 227200-33-1 |
| DIMETHICONOL MOHWA BUTTERATE | Silicones and siloxanes, dimethyl, hydroxy-terminated, esters with mowrah(mohwa)-oil fatty acids | 225233-88-5 |
| DIMETHICONOL SAL BUTTERATE | Reaction product of the fatty acids derived from Sal butter and poly[oxy(dimethylsilylene)], α-hydro-ω-hydroxy | |
| DIMETHICONOL STEARATE | | |
| DIMETHICONOL/IPDI COPOLYMER | Poly[oxy(dimethylsilylene)], α-hydro-ω-hydroxypolymer with 5-isocyanato-1-(isocyanatomethyl)-1,3,3-trimethylcyclohexane | 193281-67-3 |
| DIMETHICONOL/SILSESQUIOXANE COPOLYMER | Siloxanes and silicones, di-Me, polymers with Me silsesquioxanes, hydroxy-terminated | |
| DIMETHICONOL/STEARYL METHICONE/PHENYL TRIMETHICONE COPOLYMER | Polymer formed from poly[oxy(methylstearyl)silylene, α-trimethylsilyloxy-ω-trimethylsilyl, poly[oxy(phenyltrimethysilyloxy) silylene, α-trimethylsilyloxy-ω-trimethylsilyl, and poly[oxy(dimethylsilylene)], α-hydro-ω-hydro | |
| DIMETHOXYSILYL ETHYLENEDIAMINOPROPYL DIMETHICONE | | 71750-80-6 |
| DIMETHYLAMINOPROPYLAMIDO PCA DIMETHICONE | Polymer formed from poly[oxy(dimethyl)silylene and poly{oxy[3-{4-[({3-[dimethylamino]-propyl}-amino)carbonyl]2-oxo-1-pyrrolidinyl}propyl)methyl]}, α-trimethylsilyloxy-ω-trimethylsilyl | 179005-02-8 |
| DIMETHYLSILANOL HYALURONATE | Hyaluronic acid, dimethylsilylene ester | 128952-18-1 |
| DIPHENYL DIMETHICONE | | |
| DISODIUM DIMETHICONE COPOLYOL SULFOSUCCINATE | | |
| DROMETRIZOLE TRISILOXANE | Phenol, 2-(2H-benzotriazol-2-yl)-4-methyl-6-[2methyl-3-[1,3,3,3-tetramethyl-1-[(trimethylsilyl)oxy]disiloxanyl]- | 155633-54-8 |
| ETHYLHEXYL DIMETHICONE ETHOXY GLUCOSIDE | | |
| FLUORO C2-8 ALKYLDIMETHICONE | | |
| HEXADECYL METHICONE | | |
| HEXAMETHYLDISILOXANE | Hexamethyldisiloxane | 107-46-0 |
| HEXYL METHICONE | Poly[oxy(hexylmethylsilylene)], α-trimethylsilyl), ω-[(trimethylsilyl)oxy]- | 56746-86-2 |
| HYDROLYZED SOY PROTEIN/DIMETHICONE COPOLYOL ACETATE | Polydimethylsiloxane, copolymer with polyoxyethylene and polyoxypropylene, acetylated, reaction products hydrolyzed soy protein | |
| HYDROLYZED WHEAT PROTEIN/DIMETHICONE | Polydimethylsiloxane, copolymer with polyoxyethylene and polyoxypropylene, | |

TABLE 3-continued

| INCI[1] Name | Chemical/IUPAC[2] Name | CAS No. |
|---|---|---|
| COPOLYOL ACETATE | acetylated, reaction products hydrolyzed wheat protein | |
| HYDROLYZED WHEAT PROTEIN/DIMETHICONE COPOLYOL PHOSPHATE COPOLYMER | | |
| LAURYLMETHICONE COPOLYOL | | |
| LINOLEAMINDOPROPYL PG-DIMONIUM CHLORIDE PHOSPHATE DIMETHICONE | Proanamimium, 2,3-hydroxy-N,N-dimethyl-N-[3-(1-oxo-9,12-octadecadienylamino)propyl]-3-phosphate trieser, trichoride, reaction products with polydimethylsiloxane | 243662-49-9 |
| METHICONE | Poly(oxy(methylsilylene)] | 9004-73-3 |
| METHYLSILANOL ACETYLMETHIONATE | L-methionine, N-acetyl-, dihydroxymethylsilyl ester | 105883-43-0 |
| METHYLSILANOL ACETYL TYROSINE | L-tyrosine, N-acetyl-o-(dihydroxymethylsilyl)- | 105883-45-2 |
| METHYLSILANOL ASCORBATE | L-ascorbic acid, 6-O-(dihydroxymethylsilyl) | 187991-39-5 |
| METHYLSILANOL CARBOXYMETHYL THEOPHYLLINE | 7H-purine-7-acetic acid, 1,2,3,6-tetrahydro-1,3-dimethyl-2,6-dioxo-, dihydroxymethylsilyl ester | 105883-42-9 |
| METHYLSILANOL CARBOXYMETHYL THEOPHYLLINE ALGINATE | Reaction products of methyl-silanol carboxymethyl theophylline and alginic acid | |
| METHYLSILANOL ELASTINATE | Elastins, esters with hydroxy-terminated hydroxy Me siloxanes | 133101-79-8 |
| METHYLSILANOL GLYCYRRAHIZINATE | α-d-glucopyranosiduronic acid, (3β, 20β)-20-carboxy-11-oxo-30-norolean-12-en-3-yl-2-o-β-d-glucopyranosyl-, dihydroxymethylsilyl ester | |
| METHYLSILANOL HYDROXYPROLINE | L-proline, 5-hydroxy-, dihydroxymethylsilyl | 105883-44-1 |
| METHYLSILANOL HYDROXYPROLINE ASPARTATE | | |
| METHYLSILANOL MANNURONATE | Siloxanes and silicones, α-D-mannopyranuronoyl-oxy Me, hydroxyl-terminated | 128973-71-7 |
| METHYLSILANOL PCA | L-proline, 5-oxo-, dihydroxymethylsilyl ester | 105883-41-8 |
| METHYLSILANOL PEG-7 GLYCERYL COCOATE | Fatty acids, coco, 3-esters with polyethylene glycol dihydroxymethylsilyl 2,3-dihydroxypropyl ether | 106040-46-4 |
| METHYLSILANOL SPIRULINATE | Proteins, Spirulina, reaction products with methylsilanetriol | 188012-54-6 |
| METHYLSILANOL TRIPEG-8 GLYCERYL COCOATE | Fatty acids, coco, ester with α, α, α-(methylsilylidyne)tris (ω-(2,3-dihyrdoxypropoxy)poly(oxy-1,2-ethanediyl)) | 128973-72-8 |
| MYRISTAMIDOPROPYL DIMETHYLAMINE DIMETHICONE COPOLYOL PHOSPHATE | | 137145-36-9 |
| OCTAMETHYLTRISILOXANE | Octamethyltrisiloxane | 107-51-7 |
| PCA DIMETHICONE | 3-(4-carboxy-2-oxo-1-pyrrolidinyl)propyl methyl siloxane, polymer with dimethylsiloxane, trimethylsilyl-terminated | 179005-03-9 |
| PHENETHYL DIMETHICONE | 2-phenylethyl methyl siloxane, polymer with dimethylsiloxane, trimethylsilyl-terminated | 67762-82-7 |
| PHENETHYL DISILOXANE | Disiloxane, 1,1,2,2,2-pentamethyl-1-(2-phenylethyl)- | |
| PHENYL DIMETHICONE | 1,1,3,3-tetramethyl-1,3-diphenyldisiloxane | 56-33-7 |
| PHENYL METHICONE | | 63148-58-3 |
| PHENYL TRIMETHICONE | 1,1,5,5,5-hexamethyl-3-phenyl-3-[(trimethylsilyl)oxy]trisiloxane | 2116-84-9 |
| POLYSILICONE-1 | | |
| POLYSILICONE-10 | Polydimethylsiloxane, methyltrimethylsilyloxy-3-hydroxypropoxysilyl terminated, ethoxylated, diester with perfluroalky hydrogen dilinoleate | |
| POLYSILICONE-11 | Cyclosiloxanes, dimethyl, polymers with dimethyl, methyl hydrogen siloxanes and vinyl-group terminated dimethylsiloxanes | 226992-90-1 |
| POLYSILICONE-2 | | |
| POLYSILICONE-3 | | |
| POLYSILICONE-4 | | |

TABLE 3-continued

| INCI[1] Name | Chemical/IUPAC[2] Name | CAS No. |
|---|---|---|
| POLYSILICONE-5 | | |
| POLYSILICONE-6 | | 146632-09-9 |
| POLYSILICONE-7 | | 146632-08-8 |
| POLYSILICONE-8 | 3-thiopropyl methyl siloxane, polymer with dimethylsiloxane, ester with polymer of 2-propenoic acid and methyl 2-methyl-2-propenoate | |
| POLYSILICONE-9 | Silicones and siloxanes, 3-aminopropyl methyl, dimethyl, reaction products with 2-ethyl-4,5-dihydrooxazole homopolymer, ethyl sulfates | 165445-18-1 |
| POTASSIUM DIMETHICONE COPOLYOL PANTHENYL PHOSPHATE | | |
| POTASSIUM DIMETHICONE COPOLYOL PHOSPHATE | | |
| PVP/DIMETHICONYLACRYLATE/ POLYCARBAMYL/POLYGLYCOL ESTER | | |
| QUATERNIUM-86 | Protein hydrolizates, wheat, reaction products with acetyl chloride and ethoxylated propoxylated dimethyl siloxanes, 2-chloroethanol-quaternized | 245090-44-2 |
| SILANEDIOL SALICYLATE | 2-hydroxybenzoic acid, dihydroxysilyl ester | |
| SILANETRIOL ARGINATE | L-arginine, dihydroxymethylsilyl ester | 190270-68-9 |
| SILANETRIOL GLUTAMATE | L-glutamic acid, 5-(dihydroxymethylsilyl) ester | 190270-72-5 |
| SILANETRIOL LYSINATE | L-lysine, dihydroxymethylsilyl ester | 190270-74-7 |
| SILANETRIOL TREHALOSE ETHER | α-D-glucopyranoside, α-D-glucopyranosyl 2-O-(dihydroxymethylsilyl)- | 190270-70-3 |
| SILICA DIMETHYL SILYLATE | Silane, dichlorodimethyl-, reaction products with silica | 68611-44-9 |
| SILICA SILYLATE | | |
| SILICONE QUATERNIUM-1 | | |
| SILICONE QUATERNIUM-11 | Silicones and siloxanes, dimethyl, 3-hydroxypropyl methyl, ethers with polyethylene glycol mono[[dodecylbis(2-hydroxyethyl)ammonio]acetate], chlorides | 226992-88-7 |
| SILICONE QUATERNIUM-12 | Silicones and siloxanes, dimethyl, 3-hydroxypropyl methyl, ethers with polyethylene glycol mono[[(3-cocoamidopropyl)dimethylammonio]acetate], chlorides | 142657-60-1 |
| SILICONE QUATERNIUM-13 | Silicones and siloxanes, 3-(3-carboxy-1-oxopropoxy) methyl, dimethyl, 3-hydroxypropyl methyl, esters with (2R)-2,4-dihyrdoxy-N-(3-hydroxypropyl)-3,3-dimethylbutanamide, ethers with polyethylene glycol mono[[dimethyl[3-[(1-oxotetradecyl)amino]propyl]ammonio]acetate], chlorides | 227200-29-5 |
| SILICONE QUATERNIUM-2 | | |
| SILICONE QUATERNIUM-3 | | |
| SILICONE QUATERNIUM-4 | | |
| SILICONE QUATERNIUM-5 | | |
| SILICONE QUATERNIUM-6 | | |
| SILICONE QUATERNIUM-7 | | |
| SILICONE QUATERNIUM-8 | | |
| SILICONE QUATERNIUM-9 | | |
| SILOXANETRIOL AGLINATE | Alginic acid, esters with siloxanetriol | |
| SILOXANETRIOL PHYTATE | Silicones and siloxanes, hydroxyl Me, hydroxy-terminated, esters with myo-inositol exakis(dihydrogen phosphate) | 190454-04-7 |
| SIMETHICONE | | 8050-81-5 |
| SODIUM LACTATE METHYLSILANOL | 2-[(dihydroxymethylsilyl)oxy]propionic acid, mono sodium salt | |
| SODIUM PG-PROPYL THIOSULFATE DIMETHICONE | | |
| SORBITYL SILANDEDIOL | D-glucitol, 1,3-O-(dimethylsilylene)- | 221346-75-4 |
| STEARALKONIUM DIMTHICONE COPOLYOL PHTHALATE | Silicones and siloxanes, di-Me, ethers with ethyleneglycol, propylene glycol copolymer mono(hydrogen phthalate), N,N-dimethyl-N-octadecylbenzenemethanaminium salts | |

TABLE 3-continued

| INCI[1] Name | Chemical/IUPAC[2] Name | CAS No. |
|---|---|---|
| STEARAMIDOPROPYL DIMETHICONE | Siloxanes and silicones, dimethyl, methyl 3-[(1-oxooctadecyl)amino]propyl | 227200-31-9 |
| STEAROXY DIMETHICONE | Siloxanes and silicones, dimethyl, (octadecyloxy)-terminate | 68554-53-0 |
| STEAROXYMETHICONE/DIMETHICONE COPOLYMER | | |
| STEARYL DIMETHICONE | Siloxanes and silicones, dimethyl, methyl stearyl | 67762-83-8 |
| STEARYL METHICONE | | |
| STEARYL/AMINOPROPYL METHICONE COPOLYMER | | 110720-64-4 |
| TEA-DIMETHICONE COPOLYOL PHOSPHATE | Siloxanes and silicones, dimethyl, ethers with ethylene glycol/propylene glycol copolymer mono(dihydrogenphosphate), triethanolamine salts | |
| TETRABUTOXYPROPYL TRISILOXANE | | |
| TETRAMETHYL TETRAPHENYL TRISILOXANE | 1,3,3,5-tetramethyl-1,1,5,5-tetraphenyltrisiloxane | 3982-82-9 |
| TRIFLUOROMETHYL C1-4 ALKYL DIMETHICONE | | |
| TRIMETHYL PENTAPHENYL TRISILOXANE | | |
| TRIMETHYLSILOXYSILICATE | | |
| TRIMETHYLSILYLAMODIMETHICONE | | |
| TRIPHENYL TRIMETHICONE | | |
| TRIS(TRIBUTOXYSILOXY)METHYLSILANE | Trisiloxane, 1,1,1,5,5,5-hexabutoxy-3-methyl-[(tributoxysilyl)oxy]- | 67060-84-8 |
| VINYLDIMETHICONE | | |

[1]INCI = International Nomenclature of Cosmetic Ingredients
[2]IUPAC = International Union of Pure and Applied Chemistry It will thus be seen that the examples set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following embodiments are intended to cover all of the generic and specific features of the invention herein described and all statements of the scope of the invention which, as a matter of language, might be said to fall therebetween.

Particularly it is to be understood that in said embodiments, ingredients or compounds recited in the singular are intended to include compatible mixtures of such ingredients wherever the sense permits.

What is claimed is:

1. A method of treating body insect infestation comprising:
   (a) topically applying a chemical formulation comprising from 10 to 75% by volume of a siloxane, and a surfactant, to the insect infestation, wherein the siloxane is selected from the group consisting of propoxytetramethyl piperidinyl dimethicone, cyclomethicone, and cyclopentasiloxane; and
   (b) allowing the chemical formulation to remain on the insect infestation for a time sufficient to achieve at least 60% insect mortality.

2. The method of claim 1, wherein the chemical formulation further comprises one or more emulsifiers.

3. The method of claim 1, wherein the chemical formulation has a surface tension below about 25 dynes/centimeter at 20° C. and a viscosity above about 200 centistokes.

4. The method of claim 1, wherein the surfactant is selected from the group consisting of an anionic surfactant, an amphoteric surfactant, a non-ionic surfactant and a mixture thereof.

5. The method of claim 2, wherein the chemical formulation has a surface tension below about 25 dynes/centimeter at 20° C. and a viscosity above about 200 centistokes.

6. The method of claim 1, wherein the chemical formulation is allowed to remain on the insect infestation for a time sufficient to achieve at least 85% insect mortality.

7. The method of claim 1, wherein the chemical formulation is allowed to remain on the insect infestation for a time sufficient to achieve at least 100% insect mortality.

8. The method of claim 2, wherein the chemical formulation is allowed to remain on the insect infestation for a time sufficient to achieve at least 85% insect mortality.

9. The method of claim 2, wherein the chemical formulation is allowed to remain on the insect infestation for a time sufficient to achieve at least 100% insect mortality.

10. A method of treating body insect infestation comprising:
    (a) topically applying a chemical formulation comprising from 17.5 to 40% by volume of at least one siloxane, wherein the chemical formulation has a surface tension below about 25 dynes/centimeter at 20° C. and a viscosity above about 200 centistokes to the insect infestation; and
    (b) allowing the chemical formulation to remain on the insect infestation for a time sufficient to achieve at least 60% insect mortality.

11. The method of claim 10, wherein the chemical formulation comprises at least two siloxanes, wherein the total concentration of siloxanes in the chemical formulation is from 17.5 to 40% by volume.

12. The method of claim 10, wherein the siloxane is selected from the group consisting of dimethylpolysiloxane, propoxytetramethyl piperidinyl dimethicone, cyclomethicone, dimethicone and cyclopentasiloxane.

13. The method of claim 11, wherein the siloxanes are selected from the group consisting of dimethylpolysiloxane, propoxytetramethyl piperidinyl dimethicone, cyclomethicone, dimethicone and cyclopentasiloxane.

14. The method of claim 10, wherein the chemical formulation is allowed to remain on the insect infestation for a time sufficient to achieve at least 85% insect mortality.

15. The method of claim 10, wherein the chemical formulation is allowed to remain on the insect infestation for a time sufficient to achieve at least 100% insect mortality.

16. The method of claim 10, wherein the chemical formulation further comprises additives capable of evaporation such that the resulting siloxane concentration following evaporation of the additives is from 17.5 to 40% by volume.

17. The method of claim 11, wherein the chemical formulation further comprises additives capable of evaporation such that the resulting total siloxane concentration following evaporation of the additives is from 17.5 to 40% by volume.

18. The method of claim 2, wherein the surfactant is selected from the group consisting of an anionic surfactant, an amphoteric surfactant, a non-ionic surfactant and a mixture thereof.

* * * * *